United States Patent
An et al.

(10) Patent No.: US 12,201,413 B2
(45) Date of Patent: Jan. 21, 2025

(54) FREE BREATHING DYNAMIC CONTRAST ENHANCED (DCE) LIVER MR IMAGING

(71) Applicant: Washington University, St. Louis, MO (US)

(72) Inventors: Hongyu An, St. Louis, MO (US); Ulugbek Kamilov, St. Louis, MO (US); Sihao Chen, St. Louis, MO (US); Cihat Eldeniz, St. Louis, MO (US); Weijie Gan, St. Louis, MO (US); Jiaming Liu, St. Louis, MO (US); Tyler Fraum, St. Louis, MO (US)

(73) Assignee: Washington University, St. Louis, MO (US)

( * ) Notice: Subject to any disclaimer, the term of this patent is extended or adjusted under 35 U.S.C. 154(b) by 146 days.

(21) Appl. No.: 18/176,876

(22) Filed: Mar. 1, 2023

(65) Prior Publication Data
US 2024/0293039 A1   Sep. 5, 2024

(51) Int. Cl.
    *A61B 5/055*   (2006.01)
(52) U.S. Cl.
    CPC .... *A61B 5/055* (2013.01); *G06T 2207/20081* (2013.01); *G06T 2207/20084* (2013.01)
(58) Field of Classification Search
    CPC .......... A61B 5/055; G06T 2207/20081; G06T 2207/20084
    See application file for complete search history.

(56) References Cited

U.S. PATENT DOCUMENTS

| 11,238,975 B2 | 2/2022 | El-Baz et al. |
| 11,412,948 B2 | 8/2022 | Nayak et al. |
| 11,823,307 B2* | 11/2023 | Sandino ................ G06T 11/006 |
| 11,967,004 B2* | 4/2024 | Chen .................... A61B 5/7267 |

(Continued)

FOREIGN PATENT DOCUMENTS

| CN | 110689960 B | 1/2020 |
| CN | 110706218 B | 1/2020 |

(Continued)

OTHER PUBLICATIONS

Eldenizy et al. Phase2Phase: Respiratory Motion-Resolved Reconstruction of Free-Breathing Magnetic Resonance Imaging Using Deep Learning Without a Ground Truth for Improved Liver Imaging. Investigative Radiology 56(12):p. 809-819, Dec. 2021. (Year: 2021).*

(Continued)

*Primary Examiner* — Gregory H Curran
(74) *Attorney, Agent, or Firm* — Armstrong Teasdale, LLP

(57) ABSTRACT

A method for reconstructing dynamic contrast-enhanced (DCE) MR images includes receiving a plurality of continuous free-breathing DCE images, the plurality of images obtained with a contrast, sorting the images by identifying a respiratory phase associated with each of the continuous free-breathing DCE images, reconstructing the plurality continuous free-breathing DCE images into a 4D respiratory motion-resolved image, obtaining 3D deformable motion vector fields (MVFs), and utilizing a deep learning based (Continued)

motion transformation integrated forward-Fourier (DL-MO-TIF) model and the 3D deformable MVFs to reconstruct the DCE MR images.

20 Claims, 10 Drawing Sheets
(6 of 10 Drawing Sheet(s) Filed in Color)

(56) References Cited

U.S. PATENT DOCUMENTS

| | | | |
|---|---|---|---|
| 2022/0018924 | A1 | 1/2022 | Bai et al. |
| 2022/0323445 | A1 | 10/2022 | Peloso et al. |

FOREIGN PATENT DOCUMENTS

| | | | |
|---|---|---|---|
| CN | 112545478 | B | 3/2021 |
| CN | 113052937 | B | 6/2021 |
| CN | 113610752 | A | 11/2021 |
| CN | 113643269 | A | 11/2021 |
| CN | 113658151 | A | 11/2021 |
| CN | 113822863 | A | 12/2021 |
| CN | 114511564 | A | 5/2022 |
| CN | 114544689 | A | 5/2022 |
| CN | 114581701 | A | 6/2022 |
| CN | 114596318 | A | 6/2022 |
| CN | 114663702 | A | 6/2022 |
| CN | 114926482 | A | 8/2022 |
| CN | 114974575 | A | 8/2022 |
| WO | 2022141201 | A1 | 7/2022 |

OTHER PUBLICATIONS

Galakrishnan, Guha et al., An unsupervised Learning Model for Deformable Medical Image Registration; 2018; pp. 9252-9260.

Shan, Siyuan et al., Unsupervised End-to-end Learning for Deformable Medical Image Registration, Journal of Latex Class Files, Aug. 2015, vol. 14, No. 8, pp. 1-12.

Liu, Jiulong, et al., Rethinking medical image reconstruction via shape prior, going deeper and faster: Deep joint indirect registration and reconstruction, Medical Image Analysis, vol. 68, 2021, pp. 1-15.

De Vos, Bob D. et al., Mutual information for unsupervised deep learning image registration, SPIE, vol. 11313 2020, pp. 1-8.

\* cited by examiner

FREE BREATHING DYNAMIC CONTRAST ENHANCED (DCE) LIVER MR IMAGING

BACKGROUND

The field of the disclosure relates generally to the acquisition of magnetic resonance (MR) images, and more particularly, to systems and methods of acquiring free breathing dynamic contrast enhanced MR images.

Respiratory motion serves as one of the main challenges for acquiring MR images. During MR imaging acquisition, patients are commonly instructed to hold their breath in order to reduce the presence of motion artifacts in the images. This presents several issues. For example, instructing patients to hold their breath during imaging introduces a time constraint. Patients may hold their breath at different points in the breath cycle. If a patient is unable to hold their breath for long due to other conditions, this presents a serious issue with acquiring the images.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

The present embodiments may relate to, inter alia, systems and methods for reconstructing dynamic contrast-enhanced (DCE) MR images.

In one embodiment, a method for reconstructing dynamic contrast-enhanced (DCE) MR images includes receiving a plurality of continuous free-breathing DCE images, the plurality of images obtained with a contrast, sorting the images by identifying a respiratory phase associated with each of the continuous free-breathing DCE images, reconstructing the plurality continuous free-breathing DCE images into a 4 D respiratory motion-resolved image, obtaining 3D deformable motion vector fields (MVFs), and utilizing a deep learning based motion transformation integrated forward-Fourier (DL-MOTIF) model and the 3D deformable MVFs to reconstruct the DCE MR images.

In another embodiment, a system for reconstructing dynamic contrast-enhanced (DCE) MR images is provided, the system including at least one processor in communication with at least one memory, the at least one processor configured to receive a plurality of continuous free-breathing DCE images, the plurality of images obtained with a contrast, sort the images by identifying a respiratory phase associated with each of the continuous free-breathing DCE images, reconstruct the plurality continuous free-breathing DCE images into a 4 D respiratory motion-resolved image, obtain 3D deformable motion vector fields (MVFs), and utilize a deep learning based motion transformation integrated forward-Fourier (DL-MOTIF) and the 3D deformable MVFs to reconstruct the DCE MR images.

In another embodiment, a method for reconstructing dynamic contrast-enhanced (DCE) MR images is provided including training a deep learning based motion transformation integrated forward-Fourier (DL-MOTIF) model using severely undersampled k-space data, receiving a plurality of continuous free-breathing DCE images, and reconstructing the DCE MR images with the DL-MOTIF model.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The patent or application file contains at least one drawing executed in color. Copies of this patent or patent application publication with color drawing (s) will be provided by the Office upon request and payment of the necessary fee.

The figures described below depict various aspects of the systems and methods disclosed therein. Each figure depicts an embodiment of a particular aspect of the disclosed systems and methods, and that each of the Figures is intended to accord with a possible embodiment thereof. Further, wherever possible, the following description refers to the reference numerals included in the following Figures, in which features depicted in multiple Figures are designated with consistent reference numerals.

Figure 1A:
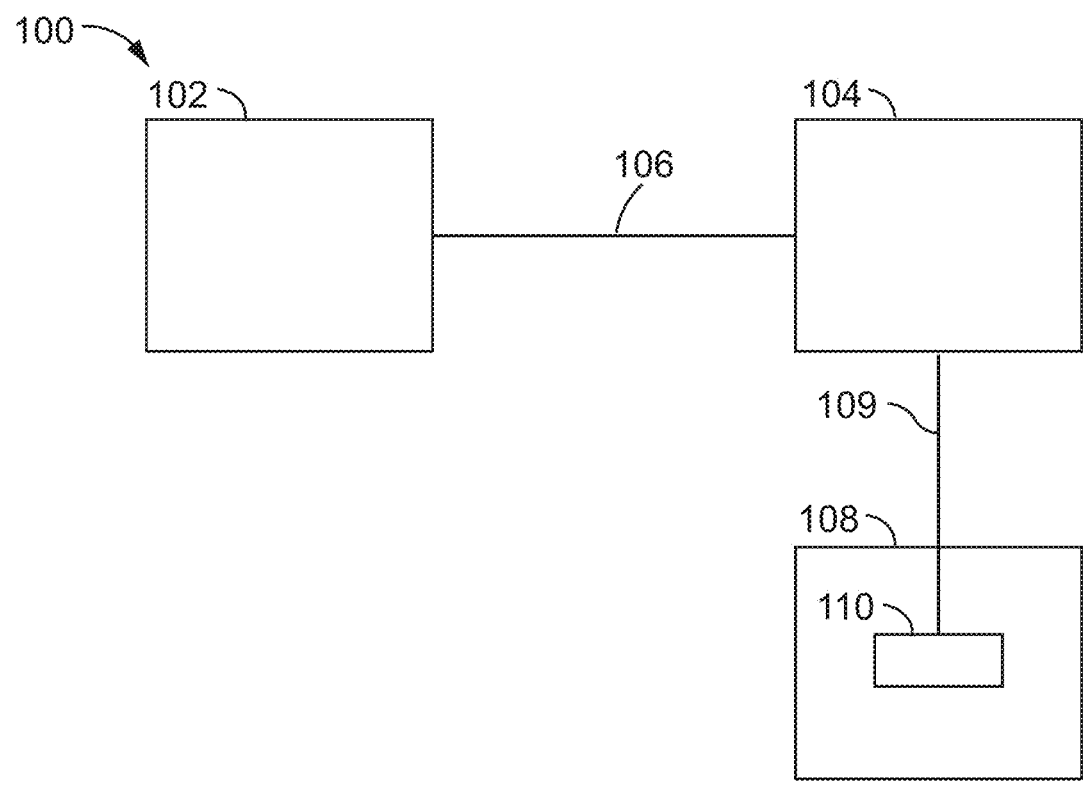

There are shown in the drawings arrangements which are presently discussed, it being understood, however, that the present embodiments are not limited to the precise arrangements and are instrumentalities shown.

FIG. 1A is a block diagram of an exemplary system.

Figure 1B:
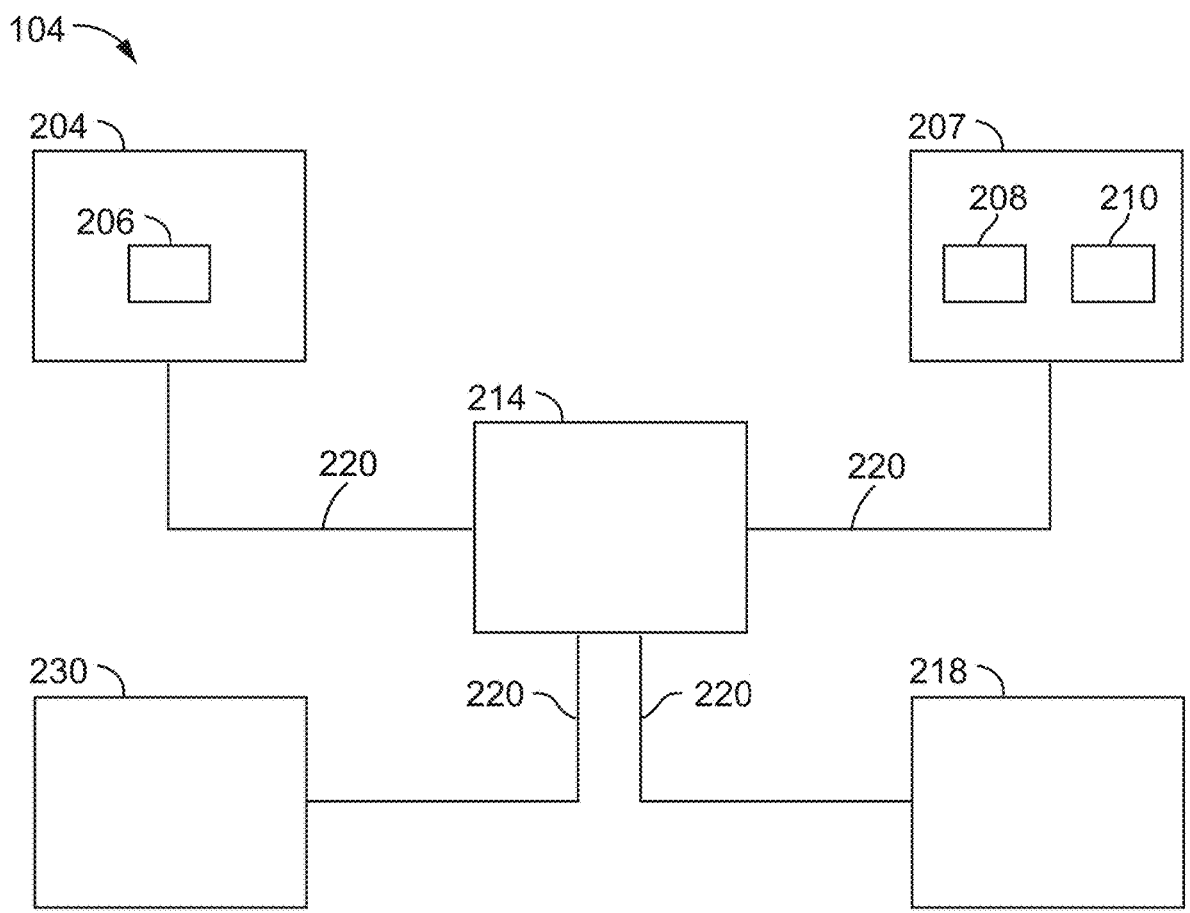

FIG. 1B is a block diagram of an exemplary computing device in the exemplary system shown in FIG. 1A.

Figure 2:
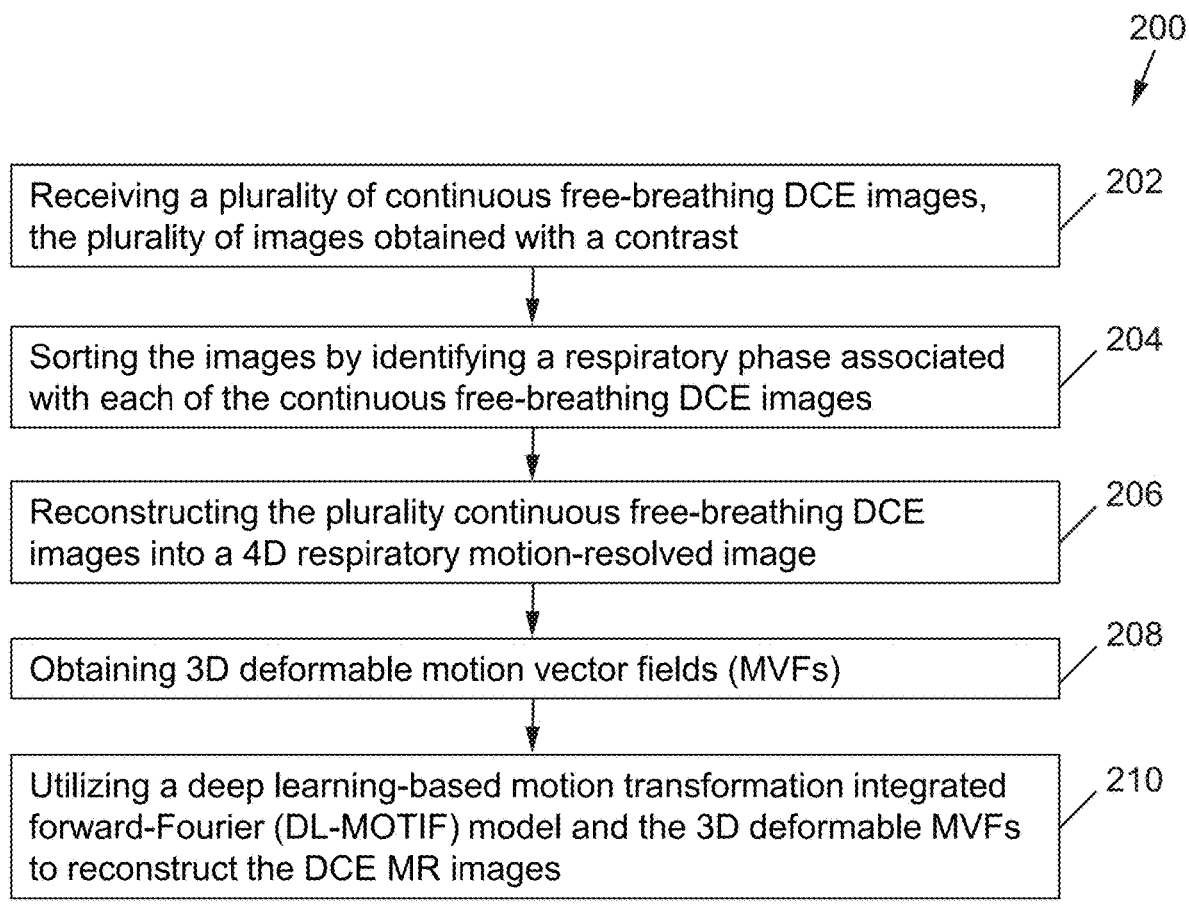

FIG. 2 is a method for reconstructing dynamic contrast-enhanced (DCE) MR images.

Figure 3:
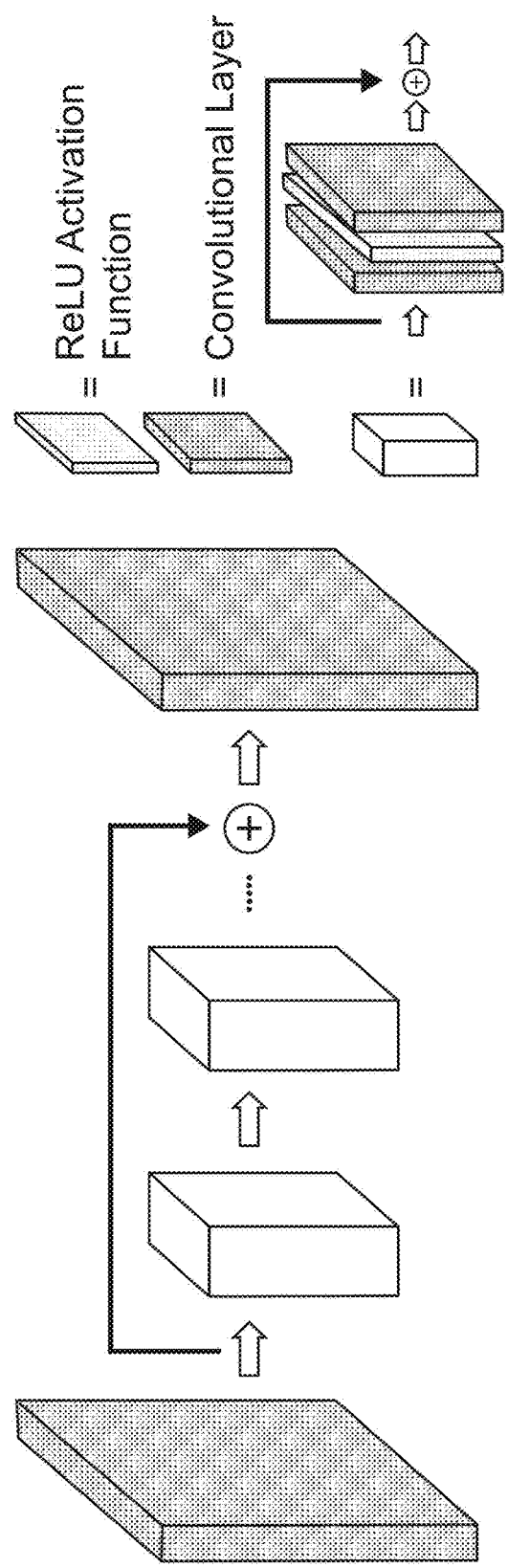

FIG. 3 illustrates the network architecture, ResNet, used for training the deep learning prior.

Figure 4:
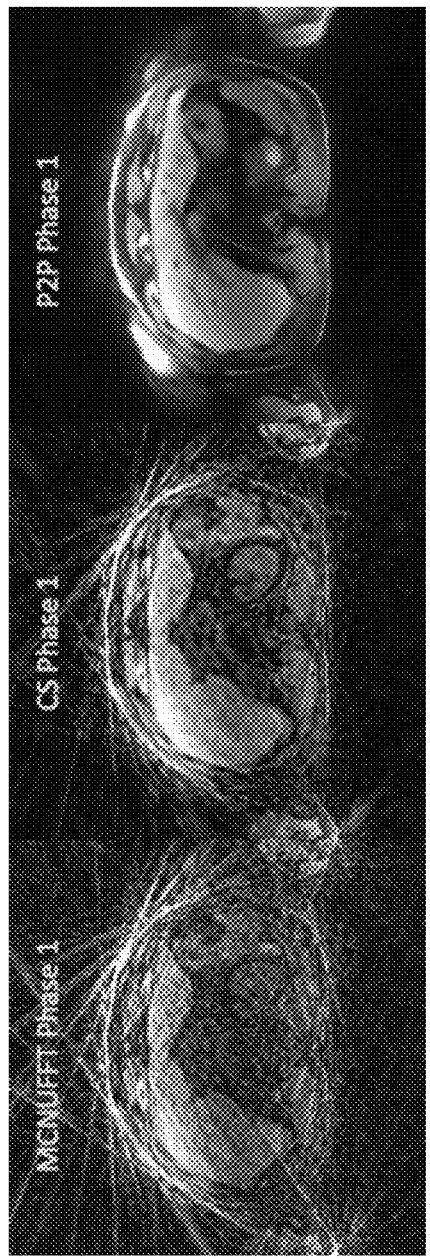

FIG. 4 shows the phase 1 (end-of-expiration) of 4 D reconstructed images (10 sec) by MCNUFFT, CS and P2P at contrast 1 (pre-contrast-injection).

Figure 5:
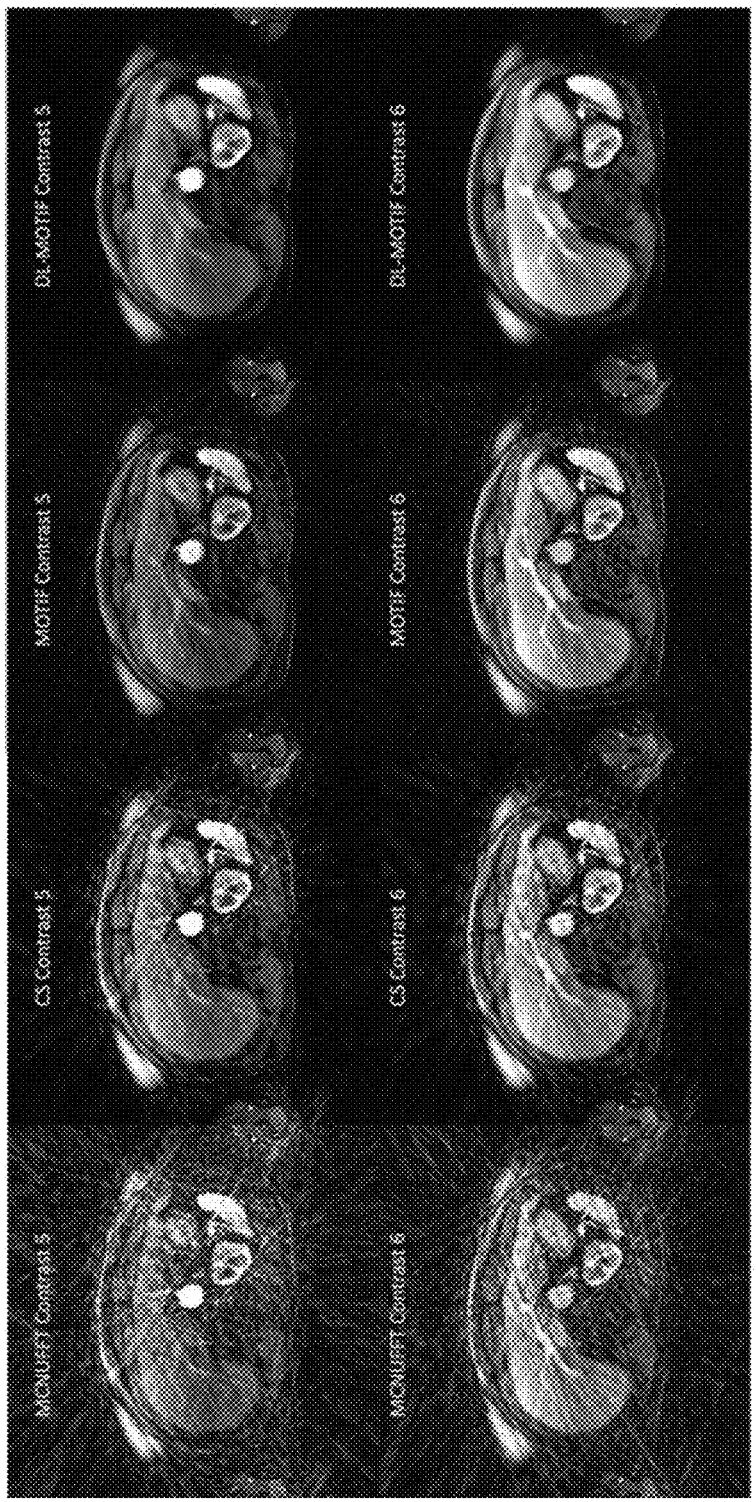

FIG. 5 shows the 3D reconstructed MCNUFFT, CS, MOTIF and DL-MOTIF images at Contrast 5 and 6 (at arterial phase) with a temporal resolution of 10 seconds for a non-oncological patient (same patient as in FIG. 3).

Figure 6:
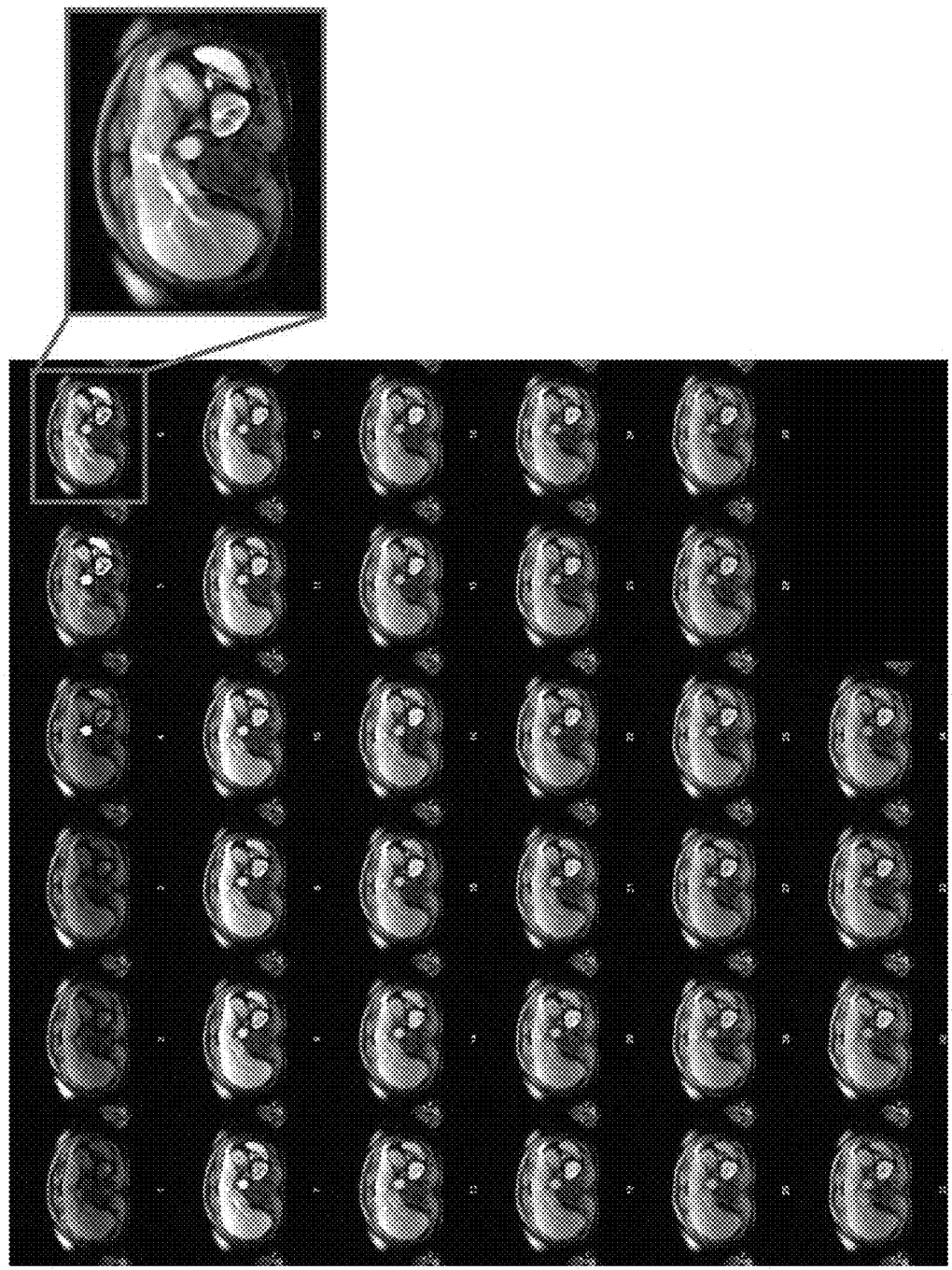

FIG. 6 shows the DL-MOTIF images across all 34 DCE contrasts.

Figure 7:
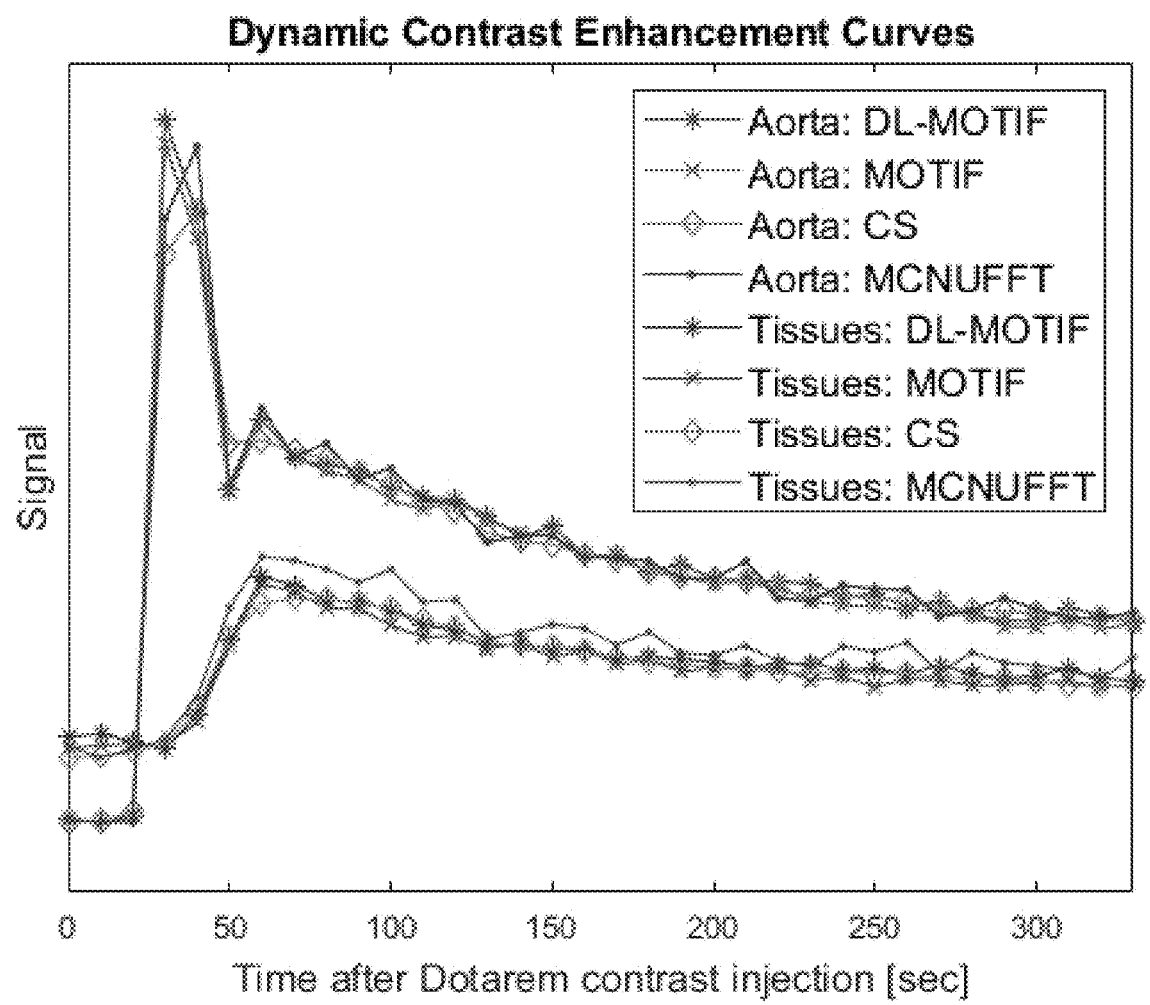

FIG. 7 shows the dynamic contrast enhancement curves on DL-MOTIF, MOTIF, MCNUFFT and CS images at aorta and normal tissues.

Figure 8:
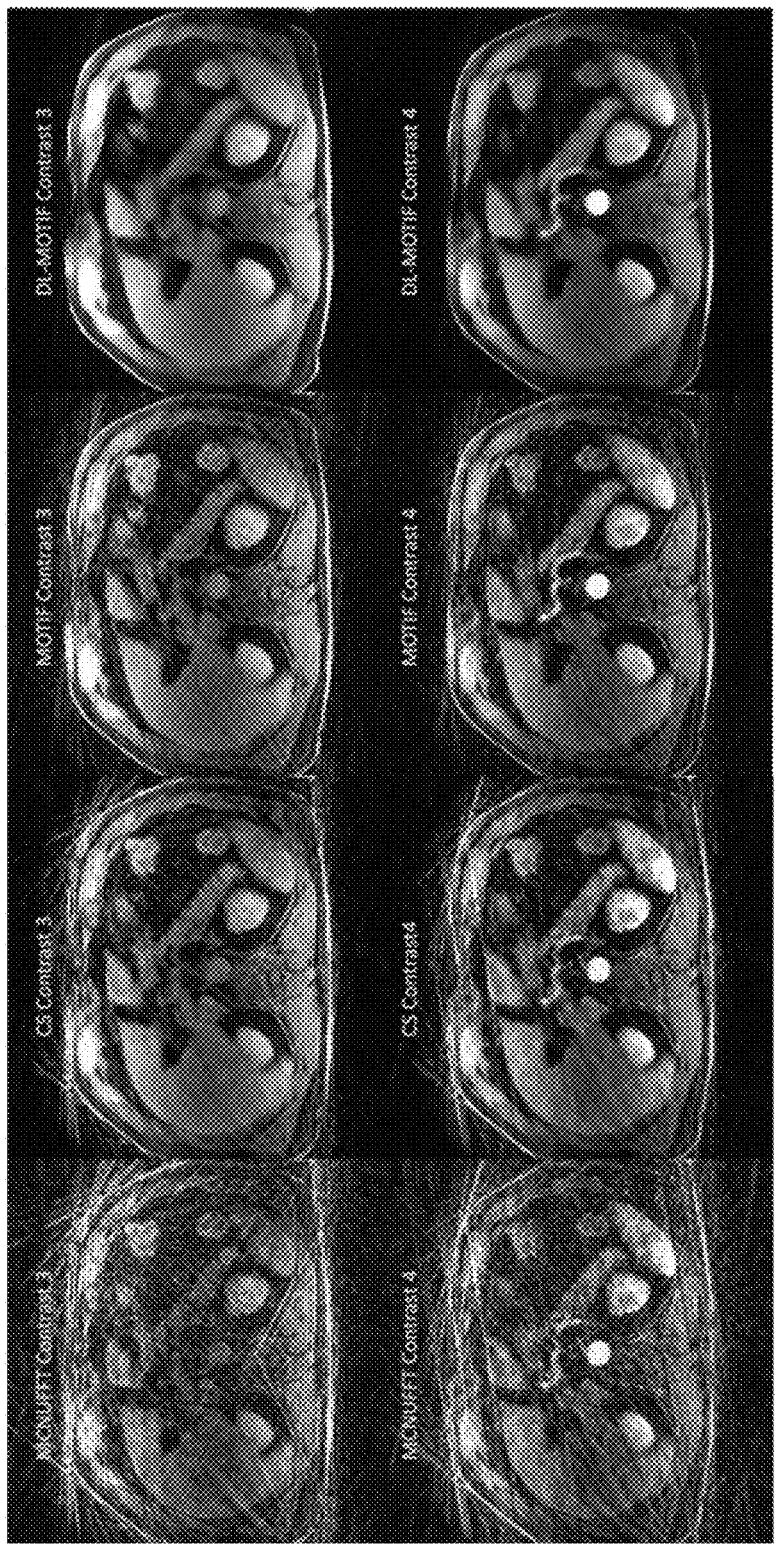

FIG. 8 shows the reconstructed MCNUFFT, CS, MOTIF and DL-MOTIF images at early arterial phase.

Figure 9:
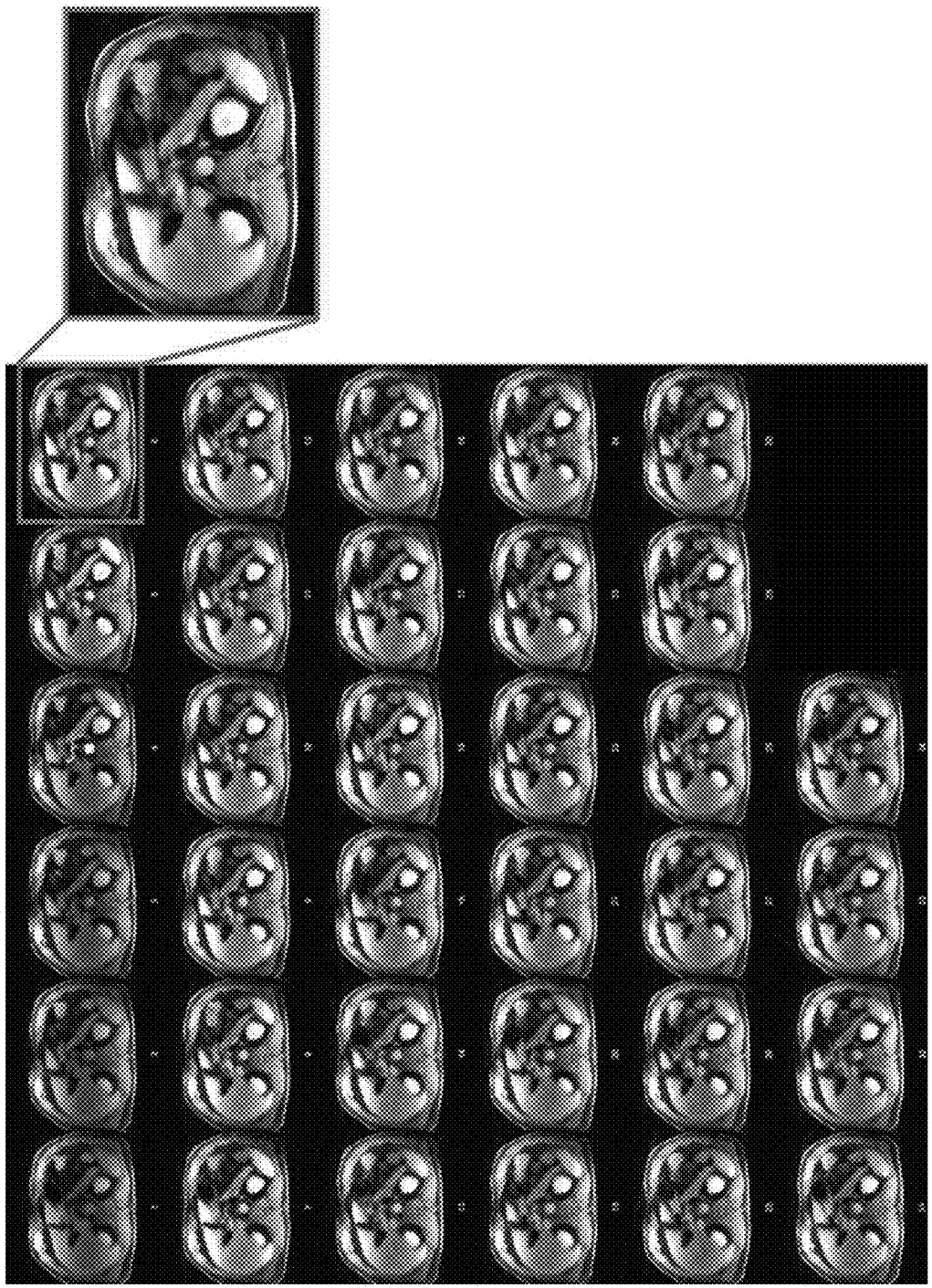

FIG. 9 shows the DL-MOTIF images across all 34 DCE contrast.

The figures depict preferred embodiments for purposes of illustration only. One skilled in the art will readily recognize from the following discussion that alternative embodiments of the systems and methods illustrated herein may be employed without departing from the principles described herein.

DETAILED DESCRIPTION

The disclosure includes systems and methods of reducing motion artifacts of free-breathing MR images of a subject. As used herein, a subject is a human, an animal, or a phantom.

MR images are frequently obtained during breath-holding. Patients are instructed to hold their breath for a time in order to obtain images without motion artifacts. However, many patients are not able to comply due to comorbid conditions, or patients may hold their breath at different stages of the breath cycle, which may result in low quality images.

Dynamic contrast enhanced MRI (DCE-MRI) is widely used for clinical diagnosis to differentiate between benign and malignant lesions. DCE-MRI techniques include acquiring a series of images before and after the injection of a contrast agent. By analyzing the concentration and flow of the contrast agent, parameters of tissue vasculature can be analyzed, and normal tissue with healthy blood flow may be differentiated from compromised tissue and vessels. Imaging may be taken with a series of contrast agents. Multiple breath hold DCE contrasts are typically obtained to capture the arterial, portal venous, and transitional phase. However, with the contrast arrival timing being unknown, a separate test-bolus scan is required to determine the exact timing of arterial, portal venous, and transitional phase. Respiratory motion artifacts are commonly present in the resultant images that are reconstructed from the multiple breath hold images.

Free breathing DCE-MRI techniques may be employed to minimize motion artifacts. Methods of reconstructing images from free-breathing DCE-MRI data are presented herein. The methods describe result in images of high quality without a need for breath-holding or a test bolus scan. The reconstruction method avoids contrast enhancement spillover from adjacent DCE contrasts.

FIG. 1A illustrates an exemplary imaging system 100. As seen in FIG. 1A, system 100 includes a sensing system 102 for imaging a subject (not shown). In one suitable embodiment, sensing system 102 is a magnetic resonance imaging device (MRI). It should be noted that the present disclosure is not limited to any one particular type of imaging and electrical technique or device, and one of ordinary skill in the art will appreciate that the current disclosure may be used in connection with any type of technique or device that enables system 100 to function as described herein.

In the exemplary embodiment, system 100 also includes a computing device 104 coupled to sensing system 102 via a data conduit 106. The computing device 104 may be representative of multiple different computing systems located at different locations, for example (i) one computing system may be involved in controlling operation of the image acquisition process and as such may be co-locating with the MRI scanning equipment, (ii) another computing system involved in communicating and storing acquired MRI image data in an image repository (database) where the image data may be retrieved for further processing (e.g., the functional mapping function), and (iii) another computing system used in performing operations on the MRI image data described herein that may be stored in the same or a different image repository, such that the output may then be accessed for use in making medical interpretations and diagnoses including use in connection with pre-operative planning and in the operating room which may involve loading the output mapping on a separate surgical navigation system. One or more of the computing systems making up the computing device 104 may, in one embodiment, comprise a picture archiving and communication system (PACS).

It should be noted that, as used herein, the term "couple" is not limited to a direct mechanical, electrical, and/or communication connection between components, but may also include an indirect mechanical, electrical, and/or communication connection between multiple components. Sensing system 102 may communicate with computing device 104 using a wired network connection (e.g., Ethernet or an optical fiber), a wireless communication means, such as radio frequency (RF), e.g., FM radio and/or digital audio broadcasting, an Institute of Electrical and Electronics Engineers (IEEE®) 802.11 standard (e.g., 802.11(g) or 802.11 (n)), the Worldwide Interoperability for Microwave Access (WIMAX®) standard, a short-range wireless communication channel such as BLUETOOTH®, a cellular phone technology (e.g., the Global Standard for Mobile communication (GSM)), a satellite communication link, and/or any other suitable communication means. IEEE is a registered trademark of the Institute of Electrical and Electronics Engineers, Inc., of New York, New York. WIMAX is a registered trademark of WiMax Forum, of Beaverton, Oregon. BLUETOOTH is a registered trademark of Bluetooth SIG, Inc. of Kirkland, Washington. Although illustrated collocated with the sensing system 102, the computing device 104 may be located remote from the sensing system 102, and may include a cloud computing device, a distributed computing device, or any other suitable computing device. Moreover, more than one computing device 104 may be used to perform the actions described herein.

System 100 also includes a data management system 108 that is coupled to computing device 104 via a network 109. Data management system 108 may be any device capable of accessing network 109 including, without limitation, a desktop computer, a laptop computer, or other web-based connectable equipment. The data management system 108 may be, or be part of, a PACS. In the exemplary embodiment, database 110 can be fully or partially implemented in a cloud computing environment such that data from the database is received from one or more computers (not shown) within system 100 or remote from system 100. Database 110 can also include any additional information of each of the subjects that enables system 100 to function as described herein.

Data management system 108 may communicate with computing device 104 using a wired network connection (e.g., Ethernet or an optical fiber), a wireless communication means, such as, but not limited to radio frequency (RF), e.g., FM radio and/or digital audio broadcasting, an Institute of Electrical and Electronics Engineers (IEEE®) 802.11 standard (e.g., 802.11(g) or 802.11(n)), the Worldwide Interoperability for Microwave Access (WIMAX®) standard, a cellular phone technology (e.g., the Global Standard for Mobile communication (GSM)), a satellite communication link, and/or any other suitable communication means. More specifically, in the exemplary embodiment, data management system 108 transmits the data for the subjects to computing device 104. While the data is shown as being stored in database 110 within data management system 108, it should be noted that the data of the subjects may be stored in another system and/or device. For example, computing device 104 may store the data therein.

FIG. 1B is a block diagram of computing device 104, which again, as discussed above, may represent multiple different computing systems performing different functions (e.g., controlling the MRI image acquisition, performing image reconstruction on acquired MRI data). In the exemplary embodiment, computing device 104 (and each of multiple different computing systems represented by device 104) includes a user interface 204 that receives at least one input from a user, such as an operator of sensing system 102 (shown in FIG. 1A). User interface 204 may include a keyboard 206 that enables the user to input pertinent information. User interface 204 may also include, for example, a pointing device, a mouse, a stylus, a touch sensitive panel (e.g., a touch pad, a touch screen), a gyroscope, an accelerometer, a position detector, and/or an audio input interface (e.g., including a microphone).

Moreover, in the exemplary embodiment, computing device 104 includes a presentation interface 207 that presents information, such as input events and/or validation results, to the user. Presentation interface 207 may also include a display adapter 208 that is coupled to at least one display device 210. More specifically, in the exemplary embodiment, display device 210 may be a visual display device, such as a cathode ray tube (CRT), a liquid crystal display (LCD), an organic LED (OLED) display, and/or an "electronic ink" display. Alternatively, presentation interface 207 may include an audio output device (e.g., an audio adapter and/or a speaker) and/or a printer.

Computing device 104 also includes a processor 214 and a memory device 218. Processor 214 is coupled to user interface 204, presentation interface 207, and to memory device 218 via a system bus 220. In the exemplary embodiment, processor 214 communicates with the user, such as by prompting the user via presentation interface 207 and/or by receiving user inputs via user interface 204. The term "processor" refers generally to any programmable system including systems and microcontrollers, reduced instruction set circuits (RISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory device 218 includes one or more devices that enable information, such as executable instructions and/or other data, to be stored and retrieved. Moreover, memory device 218 includes one or more computer readable media, such as, without limitation, dynamic random access memory (DRAM), static random access memory (SRAM), a solid state disk, and/or a hard disk. In the exemplary embodiment, memory device 218 stores, without limitation, application source code, application object code, configuration data, additional input events, application states, assertion statements, validation results, and/or any other type of data. Computing device 104, in the exemplary embodiment, may also include a communication interface 230 that is coupled to processor 214 via system bus 220. Moreover, communication interface 230 is communicatively coupled to sensing system 102 and to data management system 108 (shown in FIG. 1A).

In the exemplary embodiment, processor 214 may be programmed by encoding an operation using one or more executable instructions and providing the executable instructions in memory device 218. In the exemplary embodiment, processor 214 is programmed to reconstruct images from the MR data acquired by sensing system 102, wherein the images may be generated by processor 214 within computing device 104. The images may also be generated by an imaging device (not shown) that may be coupled to computing device 104 and sensing system 102, wherein the imaging device may generate the image based on the data received from sensing system 102 and then the imaging device may transmit the image to computing device 104 for storage within memory device 218.

During operation, sensing system 102 collects free-breathing MR data of the subject. At least one contrast is administered. Sensing system 102 transmits at least one signal representative of the data to computing device 104 via data conduit 106. More specifically, the signals are transmitted to and received by communication interface 230 within computing device 104. Communication interface 230 then transmits the signals to processor 214 for processing and/or to memory device 218, wherein the data may be stored and transmitted to processor 214 at a later time. Processor 214 may generate a reconstructed image using the free-breathing contrast enhanced MR data. Alternatively, sensing system 102 may transmit the signals to an imaging device (not shown), wherein an image may be generated. The image may then be transmitted to computing device 104, wherein the image is stored within memory device 218 and transmitted to processor 214 for processing.

Moreover, data of other subjects may be transmitted to computing device 104 from database 110 (shown in FIG. 1A) via network 109 (shown in FIG. 1). More specifically, the data may be received by communication interface 230 and then transmitted to processor 214 for processing and/or to memory device 218, wherein the data may be stored and transmitted to processor 214 at a later time. Computing device 104 may obtain the data at any time during operation.

In the exemplary embodiment, computing device 104 produces at least one reconstructed image for each of the contrasts administered. Processor 214 performs the reconstruction using a deep learning motion transformation integrated forward-Fourier (DL-MOTIF) reconstruction.

FIG. 2 is a method 200 for reconstructing dynamic contrast-enhanced (DCE) MR images. Method 200 includes receiving 202 a plurality of continuous free-breathing DCE images, the plurality of images obtained with a contrast. The plurality of continuous free-breathing DCE images may be received from the sensing system 102. Method 200 further includes sorting 204 the images by identifying a respiratory phase associated with each of the continuous free-breathing DCE images. In the exemplary embodiment, the images are sorted into 5 respiratory phases, but any number of phases may be used. Method 200 further includes reconstructing 206 the plurality continuous free-breathing DCE images into a 4 D respiratory motion-resolved image. In the exemplary embodiment, this reconstruction is performed by a P2P network. Method 200 further includes obtaining 208 3D deformable motion vector fields (MVFs). The MVFs are obtained by performing a non-linear deformable registration. Finally, utilizing 210 a deep learning based motion transformation integrated forward-Fourier (DL-MOTIF) model and the 3D deformable MVFs, the DCE MR images are reconstructed. Method 200 is repeated for each DCE contrast. In the exemplary embodiment, 34 contrasts are used with a time interval of 10 seconds. This will be described in further detail below.

Dynamic contrast-enhanced MRI (DCE-MRI) with high temporal resolution may differentiate between benign and malignant lesions. It has been widely used in clinical diagnosis and assessment of cancer, both pre- and post-therapy. Quantitative analyses of time-resolved DCE-MRI data are utilized to derive information about tumor conditions. Tracer kinetic models, such as the Tofts model and the extended Tofts model, are employed to yield physiological parameters relating to tissue perfusion and permeability.

Currently, respiratory motion serves as one of the main challenges for the acquisition of accurate DCE-MRI of the liver, leading to substantial motion artifacts and misalignment between T1-weighted DCE-MR images. The resulting misalignment is problematic for the quantitative voxel-based fitting analyses of tracer kinetic models. To minimize the issue of respiratory motion, standard-of-care (SOC) DCE is acquired during breath-holding. However, breath-hold might still be carried out at different breathing positions, causing misalignment between DCE images at different temporal points. Additionally, some patients cannot hold their breath for long often due to their comorbid conditions, limiting scan duration and image quality. The number of breath-holding instructions that can be performed along the contrast uptake curves is also limited, causing a poor temporal resolution for fitting the Tofts models.

In the exemplary embodiment, to address breath-holding issues, free-breathing DCE-MRI techniques are proposed to minimize respiratory motion artifacts. The exemplary embodiment involves DCE-MRI data being acquired continuously during free breathing using a golden-angle radial phase-encoding (GRPE) acquisition scheme. DCE-MRI images and deformable motion vector fields (MVFs) are obtained directly from the same data and motion correction is carried out during image reconstruction in an iterative way. View-sharing or compressed sensing (CS) with smoothness constrains across motion states and adjacent DCE contrasts is also proposed to reduce reconstruction artifacts. However, these techniques may lead to contrast enhancement spillover, as signal in each voxel varies not only due to the respiratory breathing position, but also due to the contrast uptake time. To address this issue, a motion transformation integrated forward-Fourier (MOTIF) reconstruction incorporating motion field derived from a Phase2Phase (P2P) reconstructed 4 D MRI is used. DCE-MRI data are acquired continuously during free-breathing using a robust self-navigated radial golden-angle stack-of-stars sequence, CAPTURE. Only data fidelity term is used in the iterative reconstruction. The exclusion of regularization term across adjacent DCE contrasts prevents contrast enhancement spillovers that could potentially introduce a bias prone to be misinterpreted by tracer kinetic models.

An image reconstruction framework, called regularization by artifact removal (RARE), effectively leverages priors learned on datasets containing only undersampled and noisy measurements. RARE framework was developed based on the concept of regularization by denoising (RED) which uses an off-the-shelf denoiser to specify an explicit regularizer that has a simple gradient. When equipped with advanced denoisers, RED leads to excellent performance in various imaging problems. RARE broadens RED beyond priors trained for the removal of additive white Gaussian noise to more general artifact removal and trains imaging priors by mapping pairs of noisy images with artifacts obtained from undersampled measurements using a Noise2Noise scheme.

The MOTIF reconstruction is expanded by including deep learning priors for regularization. The new reconstruction is named as deep learning based motion transformation integrated forward-Fourier (DL-MOTIF) and is applied to reconstruct DCE-MRI images with a temporal resolution of 10 seconds acquired using CAPTURE. The DL-MOTIF method reconstructs sharp and motion-free DCE-MRI with artifact removal on severely undersampled data. 3D motion-corrected DCE images were generated independently for each DCE contrast to avoid contrast enhancement spillover.

In the exemplary embodiment, CAPTURE, a self-navigated respiratory motion detection MR sequence, is utilized to acquire free-breathing DCE images before, during, and after contrast injection (6 minutes acquisition time) from sixteen patients using a Siemens 3T MRI scanner. However, any method may be used to obtain free-breathing DCE MR images. Eovist or Dotarem is injected 30 seconds after the start of the CAPTURE scan. The acquisition parameters were as follows: TE=1.32-1.64 ms, TR=2.82-3.5 ms, FOV=380-450 mm2, voxel size=1.25×1.25×3 mm3 or 1.4× 1.4×3 mm3, 64-80 slices, 3200-4000 radial spokes.

A free-breathing respiratory curve is obtained from CAPTURE. A 1 D navigator at a fixed azimuthal angle is consistently acquired to minimize signal contamination from system imperfections (e.g., eddy current and gradient delays). In the exemplary embodiment, the continuous free-breathing DCE images are first divided into 34 DCE contrasts with a time interval of 10 seconds. In other embodiments, any suitable number of contrasts or time interval may be used. Within each DCE contrast, the k-space data are binned into 5 respiratory phases and reconstructed into 4 D respiratory motion-resolved images by P2P. P2P network is trained using only noisy data. Non-linear deformable registration is performed to obtain 3D deformable MVFs. Symmetric normalization with mutual information as optimization metric was used for the deformable registration.

Next, the DL-MOTIF reconstruction is used to obtain the final 3D dynamic DCE-MRI for each DCE contrast. Motion correction is integrated in the image reconstruction by including a motion transformation. In short, the MVFs derived from P2P reconstruction are used in the final image reconstruction to transform all k-space data to the reference motion state (end-of-expiration). The objective function is shown below:

$$I(x, y, z) = \min_I \sum_t \sum_i \|E_{t,i}I - K_{t,i}\|_2^2 + h(I)$$

where the encoding operator $E_{ti}=F_t C_i M_t$; $F_t$ is the forward-Fourier (NUFFT) operator for each respiratory phase t; $C_i$ is the coil sensitivity for Coil i; $M_t$ are the MVFs (from P2P 4 D images) deforming the image from respiratory Phase 1 to Phase t; I is the 3D motion-corrected image; $K_{t,i}$ is the acquired k-space data for respiratory Phase t and Coil i. The deep priors are trained based on the RARE framework. The regularization is:

$$h(I) = \frac{\lambda_m}{2} I^T (I - N2N(I))$$

where $\lambda_m$ is an empirically determined constant. The N2N (I) is a deep learning denoiser on the 3D input image (I) using Noise2Noise (N2N) training strategy. The N2N network is built upon a widely used residual neural network (ResNet) architecture, but any suitable architecture may be used.

FIG. 3 illustrates the network architecture, ResNet, used for training the deep learning prior. ResNet consists of three components. The first component is a convolution layer (Conv) that takes corrupted images as input. The second component is a sequence of residual blocks. Each block alternates between a Conv followed by a rectified linear unit (ReLU), a normal Conv, and an adding residual connection. The third component is a Conv followed by an adding skip connection. It processes the feature maps generated by the first component and produces an output with the same dimension as that of the network input. Kernel sizes of all Convs are set to 3, strides to 1, and filters to 64.

In the exemplary embodiment, the prior N2N network is pre-trained using data without a high-quality ground-truth target from 10 healthy subjects for separating true signal from artifact and noise. Different binning schemes lead to different k-space coverage patterns with different acquisition times, leading to distinct patterns of undersampling streaking artifacts. Based on this observation, training data for the prior N2N network are prepared using images reconstructed from different durations and starting times by multi-coil non-uniform fast Fourier transform (MCNUFFT). Different acquisition times are obtained by splitting the dataset of ~6 minutes (~2400 spokes) of different subjects into the training dataset with 0.5, 1, 2, 3, 4, and 5 minutes. Pairs of corrupted images (phase 1: end-of-expiration) are used as the training input and target. L1-norm is used for the loss function. The network processing is based on complex-valued operations. Once the deep learning prior (a N2N network) is pre-trained. The update rule for the image reconstruction process in each iteration k with a step size γ follows:

$$I^{k+1} \leftarrow I^k - \gamma[\nabla g(I^k) + \lambda_m(I^k - N2N(I^k))]$$

Notably, DL-MOTIF is not regularized by smoothness constraints across adjacent DCE contrasts. The DL-MOTIF reconstruction is repeated for each DCE contrast, resulting in a total of 34 DCE contrasts with a temporal resolution of 10 seconds per DCE contrast. For comparison, three other reconstructions are performed: 1) baseline motion correction method: non-uniform inverse fast Fourier transform (MCNUFFT) using a respiratory efficiency window in which ⅓ of the acquisition data close to the end-of-expiration phase are used for the image reconstruction. 2) CS method: CS (using the same ⅓ of the data) with smoothness constraints across adjacent DCE contrasts, similar to commercially available (Siemens) free-breathing DCE reconstructions. Of note, motion transformation is not performed for either MCNUFFT or CS. 3) MOTIF method: DL-MOTIF reconstruction without the deep learning (DL) prior. In this reconstruction, only the data fidelity term is used in the iterative reconstruction. Motion transformation using the P2P MVFs is carried out iteratively in the MOTIF reconstruction in the same manner as DL-MOTIF, but without any regularization.

FIG. 4 shows the phase 1 (end-of-expiration) of 4 D reconstructed images (10 sec) by MCNUFFT, CS and P2P at contrast 1 (pre-contrast-injection). Example phase 1 of 4 D reconstructed images (10 sec) by MCNUFFT, CS and P2P at contrast 1 (pre-contrast-injection). MCNUFFT has severe artifacts; CS reduces streaking artifacts; P2P has the least amount of artifacts among the three, which makes it suitable for motion vector fields derivation.

FIG. 5 shows the 3D reconstructed MCNUFFT, CS, MOTIF and DL-MOTIF images at Contrast 5 and 6 (at arterial phase) with a temporal resolution of 10 seconds for a non-oncological patient (same patient as in FIG. 3). MCNUFFT image contains severe streaking artifacts; CS reduced but still suffered from streaking artifacts; MOTIF demonstrated substantial improvement on image quality and artifact removal over both MCNUFFT and CS method; by including the deep learning prior, DL-MOTIF demonstrated even further improvement on image quality and noise reduction.

Respiratory binning was performed on MCNUFFT and CS to select ⅓ of the data close to phase 1 (end-of-expiration) for motion-gated reconstruction. MCNUFFT has severe artifacts; CS reduces streaking artifacts; DL-MOTIF has the best image quality and artifact removal among the four.

FIG. 6 shows the DL-MOTIF images across all 34 DCE contrasts on the same patient. These dynamic contrasts allow radiologists to visualize DCE contrasts, including arterial, portal venous, transitional, and 5-min delay phase from a single free-breathing continuous DCE scan.

Thirty-four DCE contrasts reconstructed using DL-MOTIF on a patient. Each contrast was reconstructed using 10 seconds of non-overlapping data. Contrast 6 (at arterial phase) was zoomed in for a better visualization.

FIG. 7 shows the dynamic contrast (Dotarem) enhancement curves on DL-MOTIF, MOTIF, MCNUFFT and CS images at aorta and normal tissues. MCNUFFT showed noisy DCE signal, while CS overly smoothed dynamic signal across adjacent DCE contrasts. Both DL-MOTIF and MOTIF images effectively removed artifacts and noise, while DL-MOTIF outperformed MOTIF slightly over its shaper arterial signal peak.

Dynamic contrast enhancement curves on DL-MOTIF, MOTIF, CS and MCNUFFT at aorta and normal tissues across the entire CAPTURE duration for a patient (non-oncological). MCNUFFT showed noisy DCE signals and CS overly smoothed dynamic signal across adjacent DCE contrasts. In comparison, DL-MOTIF images effectively removed artifacts and noise, while preserving the DCE contrasts as demonstrated by the shaper arterial signal peak.

For another patient (oncological), FIG. 8 shows the reconstructed MCNUFFT, CS, MOTIF and DL-MOTIF images at early arterial phase. FIG. 9 shows the DL-MOTIF images across all 34 DCE contrast.

3D reconstructed motion-free images from an oncological patient by MCNUFFT, CS, MOTIF and DL-MOTIF at Contrast 3 and 4 (at early arterial phase) with a temporal resolution of 10 seconds. Respiratory binning was performed on MCNUFFT and CS to select ⅓ of the data close to the end-of-expiration phase for motion-gated reconstruction.

Thirty-four DCE contrasts reconstructed using DL-MOTIF on an oncological patient. Each contrast was reconstructed using 10 seconds of non-overlapping data. Contrast 6 was zoomed in for a better visualization.

As discussed above, a deep-learning based motion integrated reconstruction (DL-MOTIF) is used to reconstruct 3D high-temporal respiratory motion-resolved DCE-MRI images using a free-breathing radial acquisition. The DL-MOTIF method integrates deformable motion field information derived from the deep-learning P2P-reconstructed images and utilizes a deep-learning Noise2Noise network as prior for regularization. The DL-MOTIF method reconstructed sharp and high-quality motion-free images from severely undersampled data −14.9% of the Nyquist sampling rate for a temporal resolution of 10 seconds. To obtain accurate MVFs that describe respiratory motion, it is necessary that the intensity changes across contrast enhancement update does not affect the deformable registration. Each DCE contrast is reconstructed separately using the retrospective respiratory binning derived from CAPTURE. Therefore, temporal contrast intensity changes across different motion states are averaged out of the selected motion window (10 seconds). MVFs used in the DL-MOTIF reconstruction are first derived from the deep-learning based P2P-reconstructed 4 D-MRI. As shown by FIG. 4, P2P images demonstrated substantial improvement in image-quality (i.e., sharpness, contrast, and noise reduction) as compared to MCNUFFT and CS images. Therefore, more accurate MVFs are derived from P2P images as compared to MVFs from MCNUFFT or CS images. Then, DL-MOTIF and MOTIF both take the P2P-derived MVFs into the forward-Fourier model for motion correction. In addition to the motion-incorporated forward operator, DL-MOTIF utilizes a deep learning residual neural network as prior for regularization during the image reconstruction. The prior was pre-trained using separate human dataset to learn and remove the artifact and noise patterns from undersampled images. As a result, both DL-MOTIF and MOTIF outperformed MCNUFFT and CS method (with motion-gating from a respiratory efficiency window) in terms of image-quality and artifact-removal (FIG. 5 and FIG. 8). The improvement demonstrated the benefits of incorporating motion field transformation in the forward-Fourier model. By incorporating the deep learning prior, DL-MOTIF images demonstrates an even better improvement on image quality and artifact-freeness over MOTIF images. A clear contrast update pattern on DL-MOTIF images across DCE states for dynamic continuous DCE-MRI can be easily observed on FIG. 6 and FIG. 9. Unlike the view-sharing or CS methods, DL-MOTIF method minimizes contrast enhancement spillover from adjacent DCE contrasts as observed in FIG. 7. This allows us to derive more accurate dynamic contrast enhancement curves on DL-MOTIF images.

In at least some of the above-described embodiments, a DL-MOTIF is used as a motion correction method for dynamic free-breathing liver DCE-MRI. DL-MOTIF leverages motion integrated forward-Fourier model with deep learning prior learned from undersampled noisy data, and it allows for free-breathing continuous DCE scan, with no need for breath-hold or a test bolus to determine the exact timing of arterial, portal venous and transitional phases. The method demonstrated super image quality and artifact-freeness from severely undersampled DCE-MRI data, which allows for improved dynamic contrast enhancement quantification and easiness for diagnosis.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for reconstructing dynamic contrast-enhanced (DCE) MR images comprising:
   receiving a plurality of continuous free-breathing DCE images, the plurality of images obtained with a contrast;
   sorting the images by identifying a respiratory phase associated with each of the continuous free-breathing DCE images;
   reconstructing the plurality continuous free-breathing DCE images into a 4 D respiratory motion-resolved image;
   obtaining 3D deformable motion vector fields (MVFs); and
   utilizing a deep learning based motion transformation integrated forward-Fourier (DL-MOTIF) model and the 3D deformable MVFs to reconstruct the DCE MR images.

2. The method of claim 1, further comprising repeating the method for a plurality of contrasts.

3. The method of claim 1, wherein the plurality of continuous free-breathing DCE images are obtained using a self-navigated radial golden-angle stack-of-stars sequence.

4. The method of claim 1, wherein a temporal resolution of the DCE MR images is 10 seconds.

5. The method of claim 1, wherein the plurality of free-breathing DCE images are sorted into one of five respiratory phases.

6. The method of claim 1, wherein the DL-MOTIF utilizes a deep learning residual neural network.

7. The method of claim 1, wherein the 3D MVFs are obtained by generating Phase2Phase (P2P) reconstructed 4 D respiratory motion resolved images from the plurality of images and performing non-linear deformable registration on the 4 D motion resolved images.

8. The method of claim 1, wherein the plurality of images includes undersampled k-space data.

9. The method of claim 8, wherein a Nyquist rate of the k-space data is less than 20%.

10. A system for reconstructing dynamic contrast-enhanced (DCE) MR images, the system including at least one processor in communication with at least one memory, the at least one processor configured to:
receive a plurality of continuous free-breathing DCE images, the plurality of images obtained with a contrast;
sort the images by identifying a respiratory phase associated with each of the continuous free-breathing DCE images;
reconstruct the plurality continuous free-breathing DCE images into a 4 D respiratory motion-resolved image;
obtain 3D deformable motion vector fields (MVFs); and
utilize a deep learning based motion transformation integrated forward-Fourier (DL-MOTIF) and the 3D deformable MVFs to reconstruct the DCE MR images.

11. The system of claim 10, further comprising repeating the method for a plurality of contrasts.

12. The system of claim 10, wherein the plurality of continuous free-breathing DCE images are obtained using a self-navigated radial golden-angle stack-of-stars sequence.

13. The system of claim 10, wherein a temporal resolution of the DCE MR images is 10 seconds.

14. The system of claim 10, wherein the plurality of free-breathing DCE images are sorted into one of five respiratory phases.

15. The system of claim 10, wherein the DL-MOTIF utilizes a deep learning residual neural network.

16. The system of claim 10, wherein the 3D MVFs are obtained by generating Phase2Phase (P2P) reconstructed 4 D respiratory motion resolved images from the plurality of images and performing non-linear deformable registration on the 4 D motion resolved images.

17. The system of claim 10, wherein the plurality of images includes undersampled k-space data.

18. The system of claim 17, wherein a Nyquist rate of the k-space data is less than 20%.

19. A method for reconstructing dynamic contrast-enhanced (DCE) MR images comprising:
training a deep learning based motion transformation integrated forward-Fourier (DL-MOTIF) model using severely undersampled k-space data;
receiving a plurality of continuous free-breathing DCE images; and
reconstructing the DCE MR images with the DL-MOTIF model.

20. The method of claim 19, wherein a Nyquist rate of the k-space data is less than 20%.

* * * * *